United States Patent
McLawhorn et al.

(10) Patent No.: US 8,465,506 B2
(45) Date of Patent: Jun. 18, 2013

(54) MEDICAL DEVICES AND METHODS FOR SUTURING TISSUE

(75) Inventors: Tyler Evans McLawhorn, Winston-Salem, NC (US); Richard W. Ducharme, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 192 days.

(21) Appl. No.: 12/971,951

(22) Filed: Dec. 17, 2010

(65) Prior Publication Data

US 2011/0152891 A1   Jun. 23, 2011

Related U.S. Application Data

(60) Provisional application No. 61/289,275, filed on Dec. 22, 2009.

(51) Int. Cl.
*A61B 17/04* (2006.01)

(52) U.S. Cl.
USPC .............................. 606/145; 606/139; 606/144

(58) Field of Classification Search
USPC .......................................................... 606/145
See application file for complete search history.

(56) References Cited

U.S. PATENT DOCUMENTS

| | | | | |
|---|---|---|---|---|
| 5,766,186 A * | 6/1998 | Faraz et al. | ................... | 606/145 |
| 7,063,715 B2 * | 6/2006 | Onuki et al. | .................. | 606/220 |
| 7,615,060 B2 * | 11/2009 | Stokes et al. | .................. | 606/145 |
| 2005/0015101 A1 * | 1/2005 | Gibbens et al. | ................ | 606/144 |
| 2007/0270885 A1 * | 11/2007 | Weinert et al. | ................ | 606/139 |
| 2009/0012538 A1 * | 1/2009 | Saliman et al. | ............... | 606/145 |
| 2009/0177031 A1 * | 7/2009 | Surti et al. | .................... | 600/106 |
| 2010/0280530 A1 * | 11/2010 | Hashiba | ........................ | 606/144 |
| 2011/0112555 A1 * | 5/2011 | Overes et al. | ................. | 606/145 |

* cited by examiner

*Primary Examiner* — Corrine M McDermott
*Assistant Examiner* — Todd J Scherbel
(74) *Attorney, Agent, or Firm* — Brinks Hofer Gilson & Lione (57) ABSTRACT

Medical devices and methods are disclosed for suturing tissue, that may be employed endoscopically and/or laparoscopically, and that offer simple, reliable and controllable placement of suture around a perforation for complete closure thereof. One embodiment of the medical system generally includes an endcap having first and second arms, a needle, a suture, and first and second control members. The first and second control members are used to pass the needle back-and-forth between the first and second arms.

19 Claims, 6 Drawing Sheets

MEDICAL DEVICES AND METHODS FOR SUTURING TISSUE

CROSS-REFERENCE TO RELATED APPLICATIONS

This application claims the benefit of U.S. Provisional Application Ser. No. 61/289,275 filed on Dec. 22, 2009, entitled "MEDICAL DEVICES AND METHODS FOR SUTURING TISSUE" the entire contents of which are incorporated herein by reference.

FIELD

The present invention relates generally to medical systems, devices and procedures for suturing tissue, such as for endoscopically suturing perforations in tissue.

BACKGROUND

Openings or perforations in the walls of internal organs and vessels may be naturally occurring, or formed intentionally or unintentionally. These openings may be used to gain access to adjacent structures of the body, such techniques being commonly referred to as transluminal procedures. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies or other operations, such as tubal ligation. Many transluminal procedures for gaining access to various body cavities using other bodily lumens have also been developed. Natural orifices such as the mouth, nose, ear, anus or vagina may provide access to such bodily lumens and cavities. The bodily lumen(s) of the gastrointestinal tract are often endoscopically explored and can be utilized to provide access to the peritoneal cavity and other body cavities, all in a minimally invasive manner.

Compared to traditional open surgery or laparoscopic surgery, transluminal procedures are less invasive by eliminating abdominal incisions (or other exterior incisions) and incision related complications, while also reducing postoperative recovery time, reducing pain, and improving cosmetic appearance. At the same time, there remain challenges to transluminal procedures, including providing a suitable conduit to the openings and body cavities, robust medical devices that are maneuverable via the conduit and operable within the body cavity, sterility of the conduit, maintaining insufflation of the body cavity, proper closure of the opening, and prevention of infection. For example, when an opening is formed in a bodily wall of the gastrointestinal tract, such as in the stomach or intestines, spillage of the stomach contents, intestinal contents or other bodily fluids into the adjacent body cavity can occur. Travel of bacteria laden fluids outside of the gastrointestinal tract may cause unwanted and sometimes deadly infection.

In order to permanently close naturally occurring, intentionally or unintentionally formed perforations and allow the tissue to properly heal, numerous medical devices and methods have been developed employing sutures, adhesives, clips, tissue anchors and the like. One such class of devices aims to endoscopically close perforations, such as those within the gastrointestinal tract. Accordingly, various medical devices have been proposed that attach to the endoscope to facilitate perforation closure. Some of these medical devices employ suction to orient the tissue for suturing or anchor placement, while others require the use of tissue graspers or other devices to orient the tissue.

BRIEF SUMMARY

The present invention provides medical devices and methods for suturing a perforation in tissue, that may be used endoscopically and/or laparoscopically, and that offer simple, reliable and controllable placement of sutures around a perforation for complete closure thereof. One embodiment of a medical device, constructed in accordance with the teachings of the present invention, generally includes an endcap having first and second arms, a needle, a suture, and first and second control members. The endcap has a tubular body defining an interior space. The first arm projects from the tubular body to a first free end, and the second arm projects from the tubular body to a second free end. The first arm defines a first passageway having a first port at the first free end, and the second arm defines a second passageway having a second port and the second free end. The first and second arms are immoveably attached to the tubular body. The first and second ports spaced apart a fixed distance. The needle has first and second ends sharpened to pierce tissue, and is sized to be slidably received within the first and second passageways of the first and second arms. The needle extends over a length between the first and second ends, the length of the needle being greater than the fixed distance between the first and second ports. The suture is attached to the needle between the first and second ends of the needle. The first control member is slidably received within the first passageway of the first arm and positioned to engage the first end of the needle, wherein distal movement of the first control member moves the needle distally through the first passageway. Similarly, the second control member is slidably received within the second passageway of the second arm and positioned to engage the second end of the needle, wherein distal movement of the second control member moves the needle distally through the second passageway.

According to more detailed aspects of the medical device, the first and second passageways follow a curved path, and the needle is curved. The needle follows a needle path between the first and second arms, the needle path being curved and corresponding to the curvature of the needle. Preferably, the curved paths of the first and second passageways are semi-circular, and the needle is semi-circular. It is also preferable that the needle has a cross-sectional shape that is polygonal, and similarly the first and second passageways have a polygonal cross-sectional shape, although non-polygonal cross-sections may also be employed. For example, the needle may have a triangular cross-sectional shape.

According to further detailed aspects, the first end of the first arm preferably includes a first slot extending through the first arm to the first passageway, the first slot sized to receive the suture. Similarly, the second end of the second arm may include a second slot extending through the second arm to the second passageway, the second slot sized to receiving the suture. Preferably, the first and second slots each span a length greater than or equal to one half of the length of the needle. When the tubular body and elongate medical device define a longitudinal axis, the first and second arms are preferably spaced laterally apart on opposite sides of the longitudinal axis. The first and second control members are elongated, and further include a first engagement member located at a distal end of the first control member and a second engagement member located at a distal end of the second control member. The first and second engagement members define first and second needle pockets sized to receive the first and second ends of the needle, respectively. The first and second engagement members each include outer surfaces that preferably taper inwardly in a distal direction.

Another embodiment of a medical device for use with an elongate medical instrument, constructed in accordance with the teachings of the present invention, generally includes a an endcap having first and second arms, a needle, a suture, and first and second control members. The endcap is sized to be attached to a distal end of the elongate medical instrument, the endcap having a tubular body defining an interior space, a first arm projecting from the tubular body to a first free end, and a second arm projecting from the tubular body to a second free end. The first arm defines a first passageway having a first port at the first free end, and the second arm defines a second passageway having a second port and the second free end. The first and second passageways follow a curved path and have a polygonal cross-sectional shape. The needle has first and second ends sharpened to pierce tissue, the needle being curved and sized to be slidably received within the first and second passageways of the first and second arms. The needle also has a polygonal cross-sectional shape. The suture is attached to the needle between the first and second ends of the needle. The first control member is slidably received within the first passageway of the first arm and positioned to engage the first end of the needle. Similarly, the second control member is slidably received within the second passageway of the second arm and positioned to engage the second end of the needle.

According to more detailed aspects, the elongate medical device is preferably an endoscope, and the first and second control members are elongated and run alongside the endoscope. Preferably, the interior space and both ports can be visualized with the endoscope. The first and second passageways extending longitudinally through the tubular body to a proximal end of the tubular body. The device may further include first and second sheaths slidably receiving the first and second control members, respectively. The first and second sheaths are connected to the proximal end of the tubular body and in communication with the first and second passageways, respectively. A tissue grasper that is sized to extend through the working channel of the endoscope can grasp tissue and draw the tissue into the interior space of the tubular body of the endcap and between the first and second arms.

In yet another embodiment, in accordance with the teachings of the present invention, a method for suturing tissue is provided. The method includes providing an endoscope having a working channel extending therethrough and a tissue grasper sized to extend through the working channel. A medical device, such as those described above, are connected to the endoscope. A first area of tissue is grasped and located between the first and second arms. The first control member is moved distally to pass needle from the first passageway in the first arm, through the first area of tissue, and into the second passageway of the second arm. A second area of tissue is grasped and located between the first and second arms. The second control member is distally moved to pass needle from the second passageway in the second arm, through the second area of tissue, and into the first passageway of the first arm.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

Figure 1:
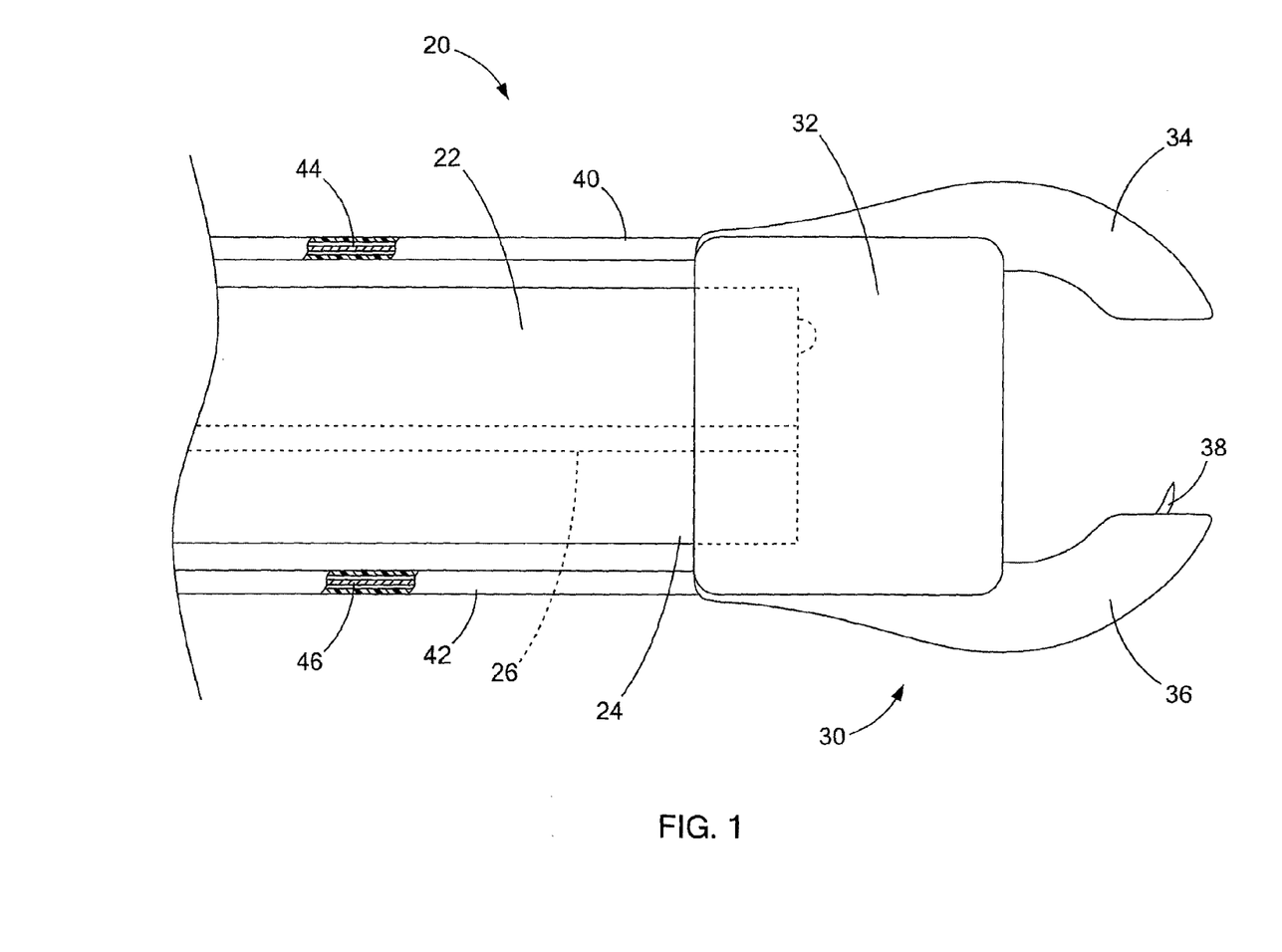
FIG. 1 is a plan view of a medical device constructed in accordance with the teachings of the present invention.

Turning now to the figures, FIG. 1 depicts a plan view of a medical device 20 for suturing tissue, constructed in accordance with the teachings of the present invention. The medical device 20 is adapted for use with an elongate medical instrument, depicted here as an endoscope 22. The endoscope 22 has a distal end 24 and a working channel 26 extending therethrough. The medical device 20 generally includes an endcap 30 that is configured to be attached to the distal end 22 of the endoscope 22, as depicted in FIG. 1.

Figure 2:
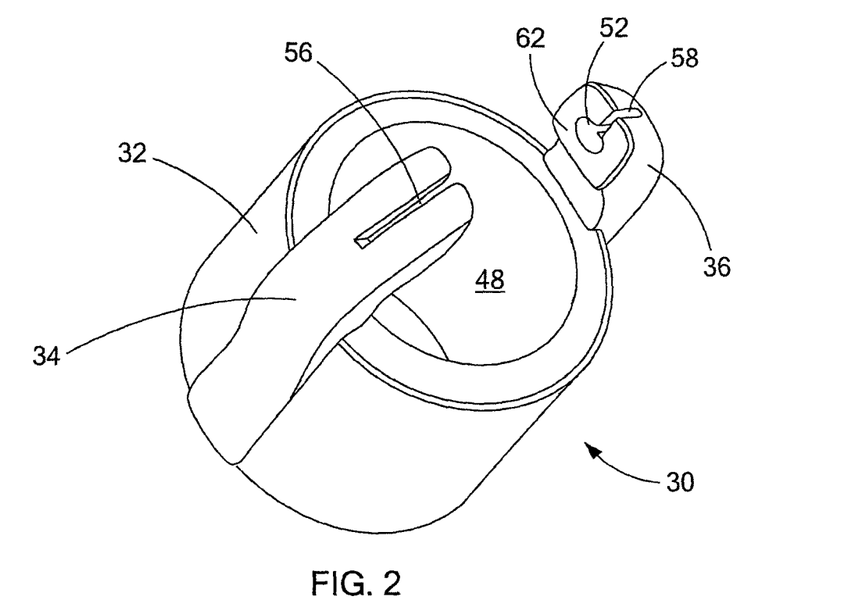
FIG. 2 is a perspective view of an end cap forming a portion of the medical device depicted in FIG. 1.
Figure 3:
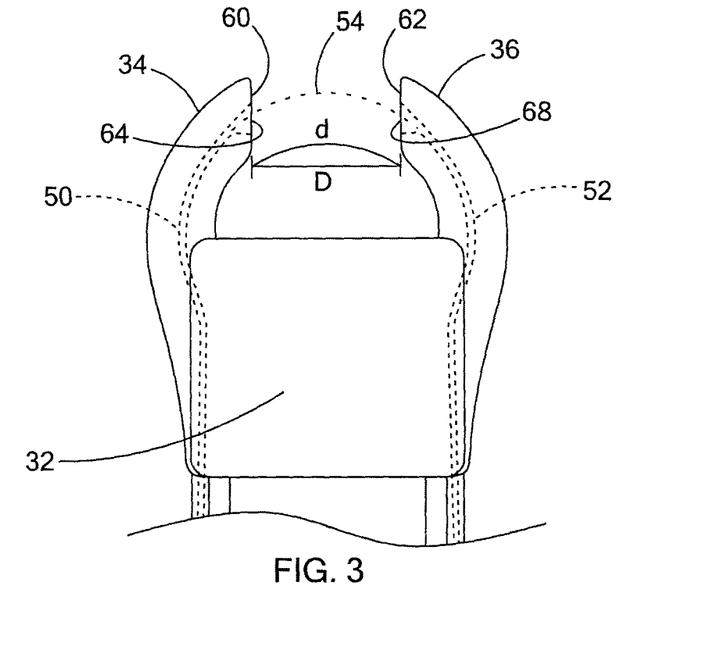
FIG. 3 is a another plan view of the medical device depicted in FIG. 1.

As best seen in FIGS. 1-3, the endcap 30 includes a tubular body 32 defining an interior space 48. The interior space 48 defined by the tubular body 32 and endcap 30 is sized to be frictionally fit on the distal end 24 of the endoscope 22, although other connection means for detachably connecting the endcap 30 to the endoscope 22 would be employed including sleeves, rings, mechanical fasteners, adhesives or other connecting means for attaching an endcap to an endoscope as is well known in the art.

The endcap also includes a first arm 34 first projecting from the tubular body 32 to a first free end, while similarly a second arm 36 projects from the tubular body 32 to a second free end. A needle 38 is adapted to be passed between the free ends of the first and second arms 34, 36 for suturing the tissue, as will be explained in further detail hereinbelow. First and second sheaths 40, 42 are connected to a proximal end of the tubular body 32 of the endcap proximate the first and second arms 34, 36, respectively. The first and second sheaths 40, 42 slidably receive first and second control members 44, 46 which extend through the sheaths 40, 42 and into the first and second arms 34, 36 for passing the needle 38 back-and-forth between the tissue for suturing the same, for example to close a perforation in the tissue.

While the medical device 20 has been described as an endcap connected an elongate medical instrument such as an endoscope 22, it will be recognized by those skilled in the art that an endoscope (or similar elongate medical device) can be integrally formed with the medical device. For example, tubular body 32, arms 34, 36, sheaths 40, 42 and the control members 44, 46 slidably contained therein could all be integrally formed in a scope. Likewise, the working channels of an endoscope, or certain lumens of a multi-lumen catheter, could be used to slidably house the control members and link them to the arts 34, 36. These and similar variations will be apparent to those skilled in the art.

As best seen in FIGS. 2 and 3, the endcap 30 includes a first passageway 50 and a second passageway 52 formed in the first and second arms 34, 36 and the tubular body 32. A distal portion of the first and second passageways 50, 52 (generally the portion corresponding with the first and second arms 34, 36) are curved and have a corresponding curvature. Accordingly, a curved path 54 is formed between the first and second passageways 50, 52, along which the needle 38 may be passed. In detail, first arm 34 projects to a distal free end defining an end surface 60 and a first port 64 of the first passageway 50. Likewise, the second arm 36 projects to a second free end defining a second end surface 62 defining a second port 66 leading to the second passageway 52. As best seen in FIGS. 2 and 3, the first and second passageways 50, 52 may taper outwardly adjacent their respect ports 64, 66 to facilitate passing the needle therebetween. The distance between the first end surface 60 and first port 64, and second end surface 62 and second port 66, can be measured as a straight line distance D or can be measured as the arcuate path d, and corresponds to the portion of the needle path 54 extending between the first and second arms 34, 36.

Figure 4:
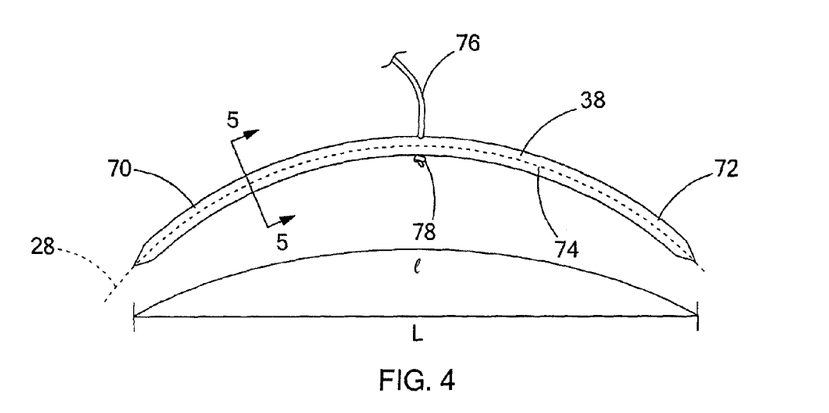
FIG. 4 is a plan view of a needle forming a portion of the medical device depicted in FIG. 1.
Figure 5:
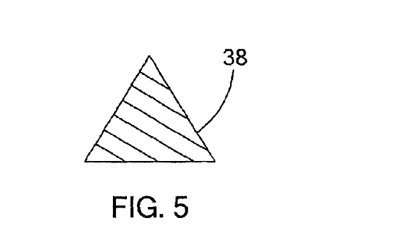
FIG. 5 is an enlarged cross-sectional view taken about the line 5-5 of FIG. 4.

As best seen in FIGS. 4 and 5, the needle 38 is curved between its first end 70 and second end 72. The first and second ends 70, 72 are preferably sharpened to pierce tissue. Between the first and second ends 70, 72, a suture 76 is attached to the needle, for example by passing the suture 76 through a bore in the needle 38 and tying a knot 78. Suitable materials for the needle 38 generally include metals such as stainless steel, alloys such as nitinol, plastics such as polyvinylchloride, polyimide, polyamide, polyetherketone and others known to those skilled in the art. The suture 36 76 may be connected via a hole or otherwise, using various means such as by tying, knots, adhesives, mechanical connectors (adjustable loops, clamps, etc.), bonding techniques such as plastic welding, melting, heat bonding and the like. Similarly, either the needle 38 or the suture 76 may be mechanically deformed, such as by crimping or using other techniques, to interconnect the suture 76 and needle 38. One end of the suture 76 is attached to the needle 38, while the other end extends proximally along the endoscope or through its working channel.

It can be seen from FIG. 4 that the needle 38 follows a curved path 28 which corresponds with the curved needle path 54 formed by the first and second passageways 50, 52 in the first and second arms 34, 36 and the space therebetween. Preferably, the needle has a length which can be measured either as an overall straight line length L, or by the arc length I defined by the curvature of the needle 38. While the passageways 50, 52, needle path 54, and needle 38 may have various curvatures, they are preferably all semi-circular in nature. Preferably, the length of the needle (L or I) is greater than the distance (D or d) between the first and second ports 64, 66 defined in the first and second end surfaces 60, 62 of the first and second arms 34, 36. The first and second passageways 50, 52 are sized to slidably receive the needle 38, and thus when the needle 38 is passed between the first and second arms 34, 36, the length of the needle 38 ensures that one or both ends 70, 72 of the needle are always contained within the first or second passageways 50, 52. In this manner, the needle 38 cannot fall out of the medical device 20 or otherwise deviate from the needle path 54 extending between the first and second arms 34, 36. Preferably, the needle 38 is constructed of a rigid material such as a metal (e.g., stainless steel, alloys such as nitinol) or plastics such as polyvinylchloride, polyimide, polyamide, polyetherketone and others known to those skilled in the art. Preferably L is greater than D and more preferably the length L is at least 20% greater than the distance D. Likewise, the length L is preferably greater than the distance d.

To further facilitate passing of the needle 38 between the first and second arms 34, 36 of the medical device 20, the needle 38 preferably has a polygonal cross-sectional shape, for example the triangular shape shown in FIG. 5. Similarly, the first and second passageways 50, 52 include a corresponding polygonal cross-section to slidably receive the needle 38. Accordingly, the needle 38 will generally not twist or rotate within the passageways 50, 52 and likewise the orientation of the suture 76 connected to the needle 38 is maintained. In this manner, the distal portions of the first and second arms 34, 36 may include slots 56, 58 which extend through the arms 34, 36 and communicate with the first and second passageways 50, 52. As such, the suture 76 may exit the arms 34, 36 via the slots 56, 58 when the needle 38 is substantially contained within the first and second arms 34, 36. The length of the slots 56, 58 is preferably about equal to or greater than one half of the length (L or I) of the needle 38. It will also be recognized that some or all of the suture 76 could also be contained within the first and second passageways 50, 52.

With reference back to FIGS. 1, 3 and 6, the medical device 20 also preferably includes control members 44, 46 extending through sheaths 40, 42, which are used to pass the needle 38 back and forth between the arms 34, 36. The control members 44, 46 have been depicted in FIG. 6 and generally include a drive wire having sufficient rigidity and strength for longitudinal force transmission, as is generally known in the endoscopic and laparoscopic fields for devices having elongate drive wires. The drive wires may be monofilament or multifilament wires, the latter of which may be wound, braided, woven, wrapped, or otherwise joined to form a wire. See, e.g., U.S. Pat. No. 5,330,482, the entire disclosure of which is incorporated herein by reference. The distal end of the control members 44, 46 include an engagement member 80 at their distal ends, the engagement member 80 defining a pocket 82 at the distal end surface which is shaped to receive the sharpened end 70, 72 of the needle 38. Preferably an outer surface of the engagement members 80 are angled and taper inwardly (in the distal direction) to facilitate passing the needle 38 in the control member 44, 46 through the tissue.

Figure 6:
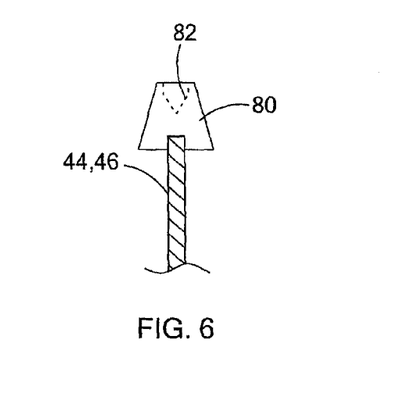
FIG. 6 is a cross-sectional view of a control member forming a portion of the medical device depicted in FIG. 1.

The engagement members 80 may also be formed as grasping devices to grasp onto the needle 38 within the passageways 50, 52. Many such mechanical grasping devices are known in the art, e.g. grasping forceps, clamps, snares, and grasping wires, and similarly electrical, electro-mechanical, and magnetic grasping devices may also be employed. As one example, the engagement members 80 may be comprised as magnets, and the ends of the needle 38 formed of a metal (ferro-magnetic), magnets, or otherwise be magnetized to be firmly retained by the control members 44, 46. With a passive or actuable grasping device, the needle 38 may be securely retained within one of the passageways 50, 52 while the operator/physician maneuvers the endoscope 22 and/or medical device 20 relative to the tissue T between passes of the needle 38.

Figure 7:
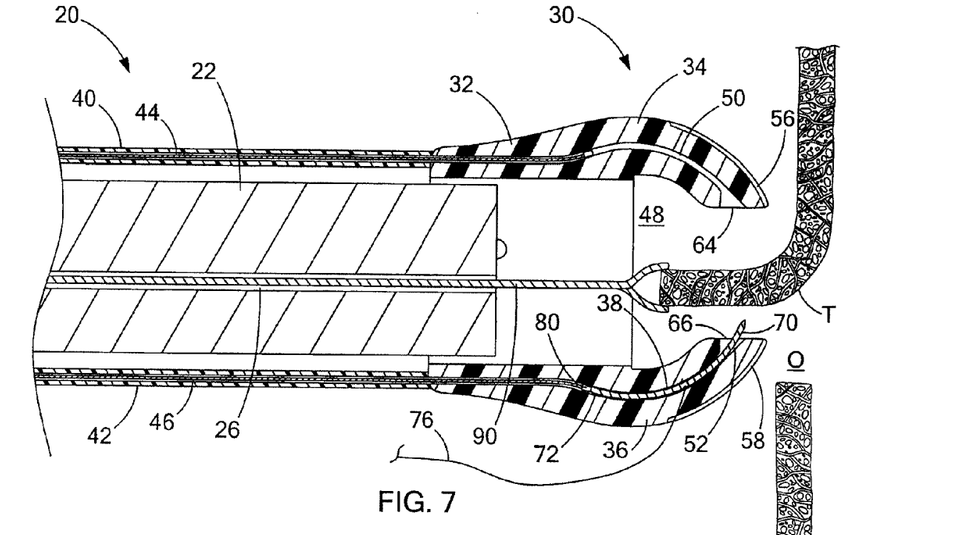
FIG. 7 is a cross-sectional view of the medical device depicted in FIG. 1 and illustrating operation of the device.

As best seen in FIG. 7, the control members 44, 46 extend through their respective sheaths 40, 42 and through the first and second passageways 50, 52 formed in the tubular body 32 and the first and second arms 34, 36. As shown in FIG. 7, the engagement member 80 of the second control member 46 abuts the second end 72 of the needle 38 which is substantially contained within the second arm 36. According to one embodiment of the methods of suturing tissue, in accordance with the teachings of the present invention, a tissue grasper 90 is passed through the working channel 26 of the endoscope 22 and used to grasp the tissue. As one example, this may be done when the tissue T has a perforation or opening O therein which needs to be closed. A grasper 90 has been shown in simplified form in FIGS. 7-10, but may be any now known or future device for grasping tissue, including forceps, piercing devices such as cork-screws or forks, graspers, clamps, pinchers, suction devices, anchors or the like.

As shown in FIG. 7, the tissue T is grasped with the grasping device 90 and drawn into the interior space 48 and between the first and second arms 34, 36 of the medical device 20. Although the needle 38 is shown having a first end 70 slightly exiting the port 66, it may be entirely contained within the second passageway 52, of the second arm 36.

Figure 8:
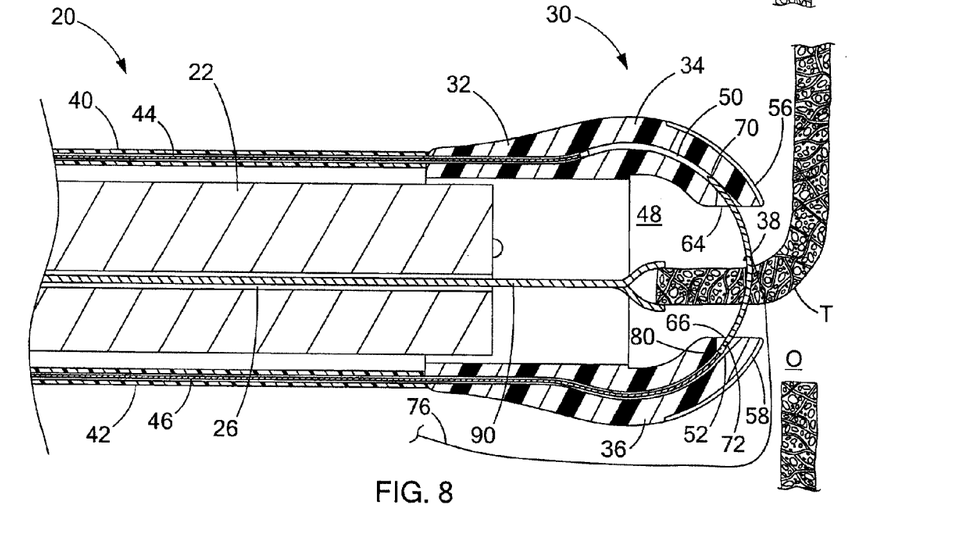
FIG. 8 is a cross-sectional view of the medical device depicted in FIG. 1 and illustrating operation of the device.
Figure 9:
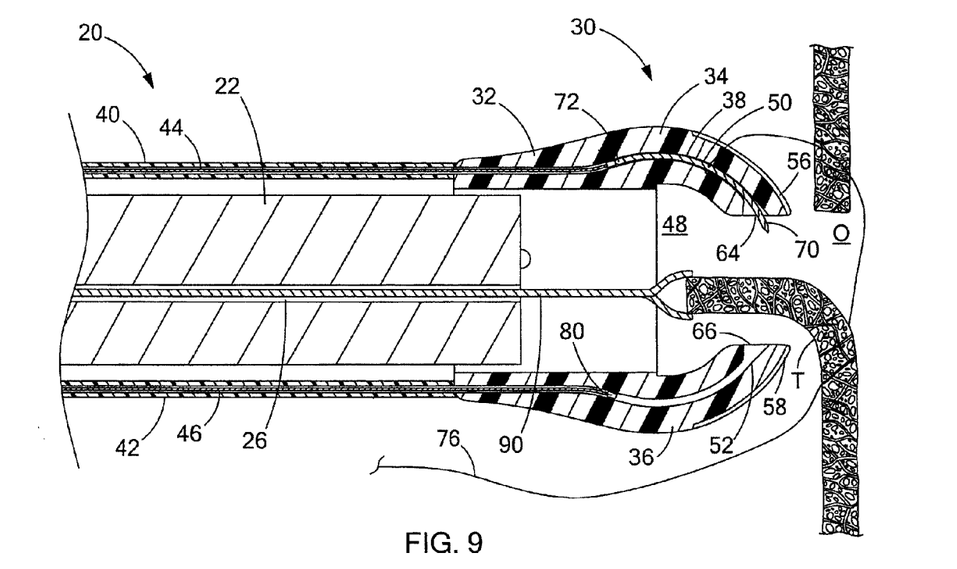
FIG. 9 is a cross-sectional view of the medical device depicted in FIG. 1 and illustrating operation of the device.

As shown in FIG. 8, the second control member 46 is advanced distally to pass the needle from the second passageway 52, through a first area of the tissue T, and into the first passageway 50 of the first arm 34 via the first port 64. Notably, as the needle 38 passes through the tissue T, so does the suture 76 attached thereto. As shown in FIG. 9, once the needle 38 has been fully passed through the tissue T, the grasped tissue T can be released and the second control member 46 retracted proximally into the passageway 52. Then, as also shown in FIG. 9, a second area of tissue T may be grasped and drawn into the interior space 48 and between the first and second arms 34, 36. Then, the first control member 44 may be advanced distally to pass the needle from the first passageway 50, through the second area of the tissue T and back into the second passageway 52 of the second arm 36 via the second port 66.

Figure 10:
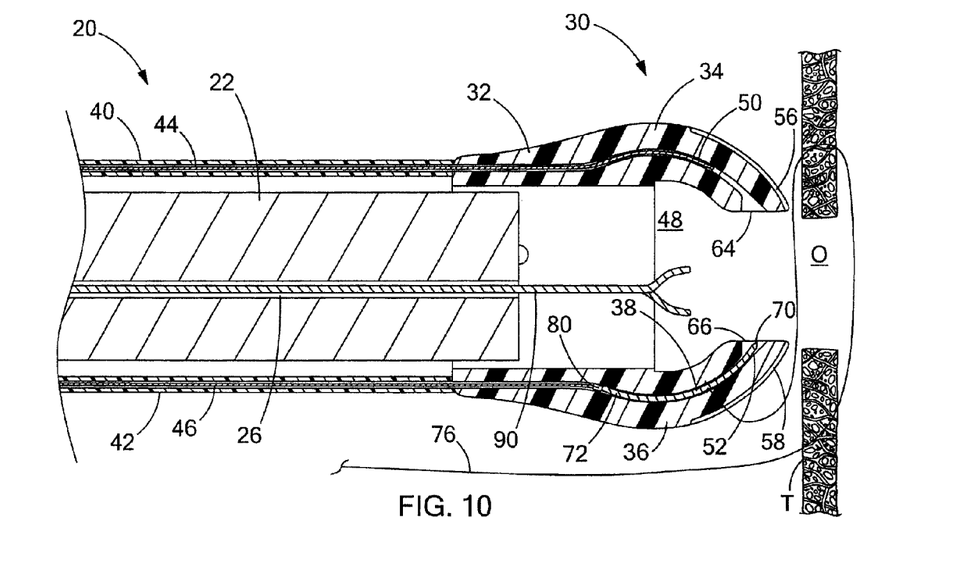
FIG. 10 is a cross-sectional view of the medical device depicted in FIG. 1 and illustrating operation of the device.

As best seen in FIG. 10, with these two passes the suture 78 has been placed through two areas of the tissue T around the opening O. The needle 38 may be contained within either of the passageways 50, 52 when moving the medical device 20 between different areas of the tissue, or during introduction or removal of the entire device from the patient. It will also be recognized that medical device 20 of the present invention may be used to weave a suture back and forth around the periphery of an opening O and tissue T so that the free ends of the suture be synched to close the opening O in a purse string fashion.

Figure 11:
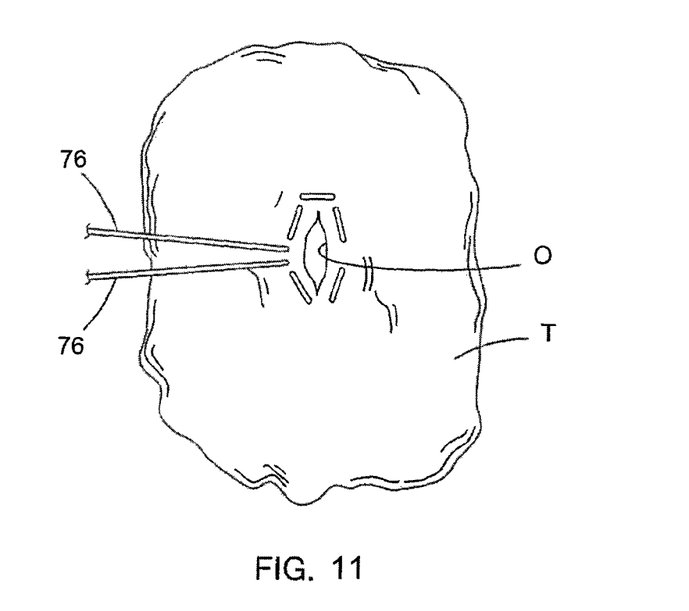
FIG. 11 is a plan view of tissue having a perforation being sutured using the medical device depicted in FIGS. 1-10.
Figure 12:
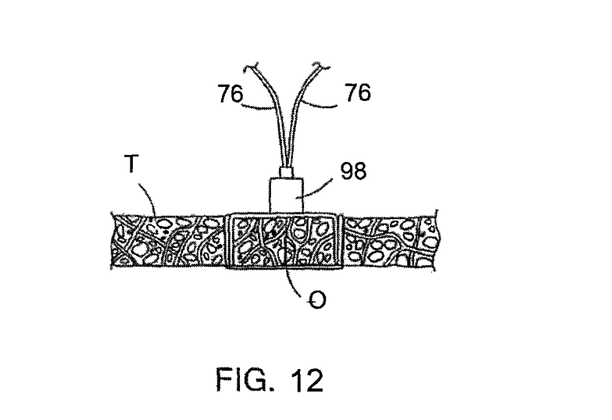
FIG. 12 is a cross-sectional view showing closure of the perforation in tissue depicted in FIG. 11.

In this manner, the suture 78 may be weaved through the tissue T and around the opening O by repeating the above-described steps, as shown in FIG. 11. The suture 36 may follow a generally annular path round the periphery of the opening O, or may criss-cross back and forth from opposing sides of the opening O. In either case, the medical device 20 is withdrawn from the patient, thereby withdrawing the needle 38 and one end of the suture 76. Accordingly, both ends of the suture 76 will be available to the medical professional and may be used to draw the opening O closed, as shown in FIG. 12. Generally, the suture 76 has been passed through the tissue T in a purse-string fashion, whereby pulling proximally on the ends of the suture 76 will naturally cause the opening O to close. The ends of the suture 76 may be tied utilizing endoscopic tying techniques including passing knots, or a suture lock 98 may be employed as is known in the art. Exemplary suture locks are described in U.S. patent application Ser. No. 12/125,525 filed May 22, 2008 and Ser. No. 12/191,001 filed Aug. 13, 2008, the disclosures of which are hereby incorporated by reference in their entirety.

Based on the foregoing it will be recognized by those skilled in the art that the medical systems, devices and methods of the present invention facilitate improved closure of perforations. The medical systems and devices are simple to operate, and the methods may be performed endoscopically and/or laparoscopically without removing the medical device 20 every time a pass is made through the tissue. The devices and methods offer reliable and controllable placement of suture(s) around a perforation for complete and reliable closure thereof.

It will also be recognized by those skilled in the art that, while the methods described above generally include placing the suturing tools in tissue through an internal bodily lumen, it will be recognized that the systems, devices and methods may be used on any layer of material (e.g. fabrics, cloth, polymers, elastomers, plastics and rubber) that may or may not be associated with a human or animal body and a bodily lumen. For example, the systems, devices and methods can find use in laboratory and industrial settings for placing devices through one or more layers of material that may or may not find application to the human or animal body, and likewise closing holes or perforations in layers of material that are not bodily tissue. Some examples include sewing or stitching and related manufacturing, working with synthetic tissues, connecting or repairing polymeric sheets, animal studies, veterinary applications, and post-mortem activities.

The foregoing description of various embodiments of the invention has been presented for purposes of illustration and description. It is not intended to be exhaustive or to limit the invention to the precise embodiments disclosed. Numerous modifications or variations are possible in light of the above teachings. In one variation, the distal grip system could be pivotally attached to the endcap and the needle driven through an arc via an actuating mechanism operated at a proximal end of the device. Appropriate guides, supports and the proximal grip system may be designed to pass the needle back and forth between the distal grip system. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for suturing tissue, the medical device comprising:

a tubular body defining an interior space, a first arm projecting from the tubular body to a first free end, and a second arm projecting from the tubular body to a second free end;

the first arm defining a first passageway having a first port at the first free end, the second arm defining a second passageway having a second port at the second free end the first and second arms immoveably attached to the tubular body such that the first and second ports are spaced apart a fixed distance;

a needle having first and second ends shaped to pierce tissue, the needle sized to be slidably received within the first and second passageways of the first and second arms; the needle extending over a length between the first and second ends, the length of the needle being greater than the fixed distance between the first and second ports;

a suture attached to the needle between the first and second ends of the needle;

a first control member slidably received within the first passageway of the first arm and positioned to engage the first end of the needle, distal movement of the first control member moving the needle distally through the first passageway, the first control member elongated such that it projects proximally out from the tubular body; and a second control member slidably received within the second passageway of the second arm and positioned to engage the second end of the needle, distal movement of the second control member moving the needle distally through the second passageway, the second control member elongated such that it projects proximally from the tubular body.

2. The medical device of claim 1, wherein the first and second passageways follow a curved path, and wherein the needle is curved.

3. The medical device of claim 2, wherein the needle follows a needle path between the first and second arms, the needle path being curved and corresponding to the curvature of the needle.

4. The medical device of claim 2, wherein the curved paths of the first and second passageways are semi-circular, and wherein the needle is semi-circular.

5. The medical device of claim 1, wherein the needle has a cross-sectional shape that is polygonal, and wherein the first and second passageways have a polygonal cross-sectional shape corresponding to the polygonal cross-sectional shape of the needle such that the needle is restricted from rotating within the first and second passageways.

6. The medical device of claim 5, wherein the needle has a triangular cross-sectional shape.

7. The medical device of claim 1, wherein the first end of the first arm includes a first slot extending through the first arm to the first passageway, the first slot sized to receive the suture, and wherein the second end of the second arm includes a second slot extending through the second arm to the second passageway, the second slot sized to receiving the suture.

8. The medical device of claim 7, wherein the first and second slots each span a length greater than or equal to one half of the length of the needle.

9. The medical device of claim 1, wherein the tubular body defines a longitudinal axis, and wherein the first and second arms are spaced laterally apart on opposite sides of the longitudinal axis.

10. The medical device of claim 1, further comprising a first engagement member located at a distal end of the first control member and a second engagement member located at a distal end of the second control member, the first and second engagement members defining first and second needle pockets sized to receive the first and second ends of the needle, respectively.

11. The medical device of claim 10, wherein the first and second engagement members each include outer surfaces that taper inwardly in a distal direction.

12. The medical device of claim 1, wherein the first and second control members are independently operable.

13. A medical device for use with an elongate medical instrument for suturing tissue, the medical device comprising:

an endcap sized to be attached to a distal end of the elongate medical instrument, the endcap having a tubular body defining an interior space, a first arm projecting from the tubular body to a first free end, and a second arm projecting from the tubular body to a second free end;

the first arm defining a first passageway having a first port at the first free end, the second arm defining a second passageway having a second port at the second free end the first and second passageways following a curved path and having a polygonal cross-sectional shape;

a needle having first and second ends sharpened to pierce tissue, the needle being curved and sized to be slidably received within the first and second passageways of the first and second arms; the needle having a polygonal cross-sectional shape corresponding to the polygonal cross-sectional shape of the first and second passageways and sized relative thereto such that the needle is restricted from rotating within the first and second passageways;

a suture attached to the needle between the first and second ends of the needle;

a first control member slidably received within the first passageway of the first arm and positioned to engage the first end of the needle; and a second control member slidably received within the second passageway of the second arm and positioned to engage the second end of the needle, wherein the first and second passageways extend longitudinally through the tubular body to a proximal end of the tubular body.

14. The medical device of claim 13, wherein the first and second ports spaced apart a fixed distance, and wherein the needle extends over a length between the first and second ends, the length of the needle being greater than the fixed distance between the first and second ports.

15. The medical device of claim 13, wherein the elongate medical instrument is an endoscope, and wherein the first and second control members are elongated and run alongside the endoscope.

16. The medical device of claim 15 wherein the interior space and both ports can be visualized with the endoscope.

17. The medical device of claim 13, further comprising first and second sheaths slidably receiving the first and second control members, respectively, the first and second sheaths connected to the proximal end of the tubular body and in communication with the first and second passageways, respectively.

18. The medical device of claim 13, wherein the elongate medical instrument is an endoscope having a working channel extending therethrough, and further comprising a tissue grasper sized to extend through the working channel and configured to grasp tissue and draw the tissue into the interior space of the tubular body of the endcap and between the first and second arms.

19. The medical device of claim 13, wherein the interior space extends longitudinally entirely through the tubular body.

* * * * *